United States Patent [19]
Fleer

[11] Patent Number: 5,057,015
[45] Date of Patent: Oct. 15, 1991

[54] DENTAL HANDPIECE HAVING AN ARRANGEMENT TO FORM COMPATIBLE CONNECTIONS TO DIFFERENTLY DESIGNED ROTATABLE JOINTS

[75] Inventor: Otto Fleer, Bensheim, Fed. Rep. of Germany

[73] Assignee: Siemens Aktiengesellschaft, Munich, Fed. Rep. of Germany

[21] Appl. No.: 431,247

[22] Filed: Nov. 3, 1989

[30] Foreign Application Priority Data

Nov. 14, 1988 [EP] European Pat. Off. ........ 88118978.1

[51] Int. Cl.$^5$ .............................................. A61C 1/08
[52] U.S. Cl. ....................................... 433/126; 433/29
[58] Field of Search .................... 433/126, 84, 29, 146, 433/82

[56] References Cited

U.S. PATENT DOCUMENTS 4,080,737 3/1978 Fleer ........................................ 32/22
4,353,697 10/1982 Nakanishi ............................ 433/126
4,403,959 9/1983 Hatakeyama ....................... 433/126
4,504,227 3/1985 Lohn ................................... 433/126
4,626,210 12/1986 Malata et al. ......................... 433/29
4,655,709 4/1987 Fleer ...................................... 433/29

FOREIGN PATENT DOCUMENTS

WO85/00281 1/1985 PCT Int'l Appl. .

Primary Examiner—Cary E. O'Connor
Attorney, Agent, or Firm—Hill, VanSanten, Steadman & Simpson

[57] ABSTRACT

A dental handpiece which can be adapted to different types of rotatable joints without great structural changes comprises a handpiece design having a sleeve-shaped end section which receives an insert part. The insert part has an outer shape that is matched to the interior of the sleeve-shaped section of the handpiece but will have an inner contour which is matched to a particular plug member of a particular type of rotatable joint. Thus, by changing the sleeve insert parts, the handpiece can be modified to receive a different type of plug member of a different type of rotatable joint.

17 Claims, 2 Drawing Sheets

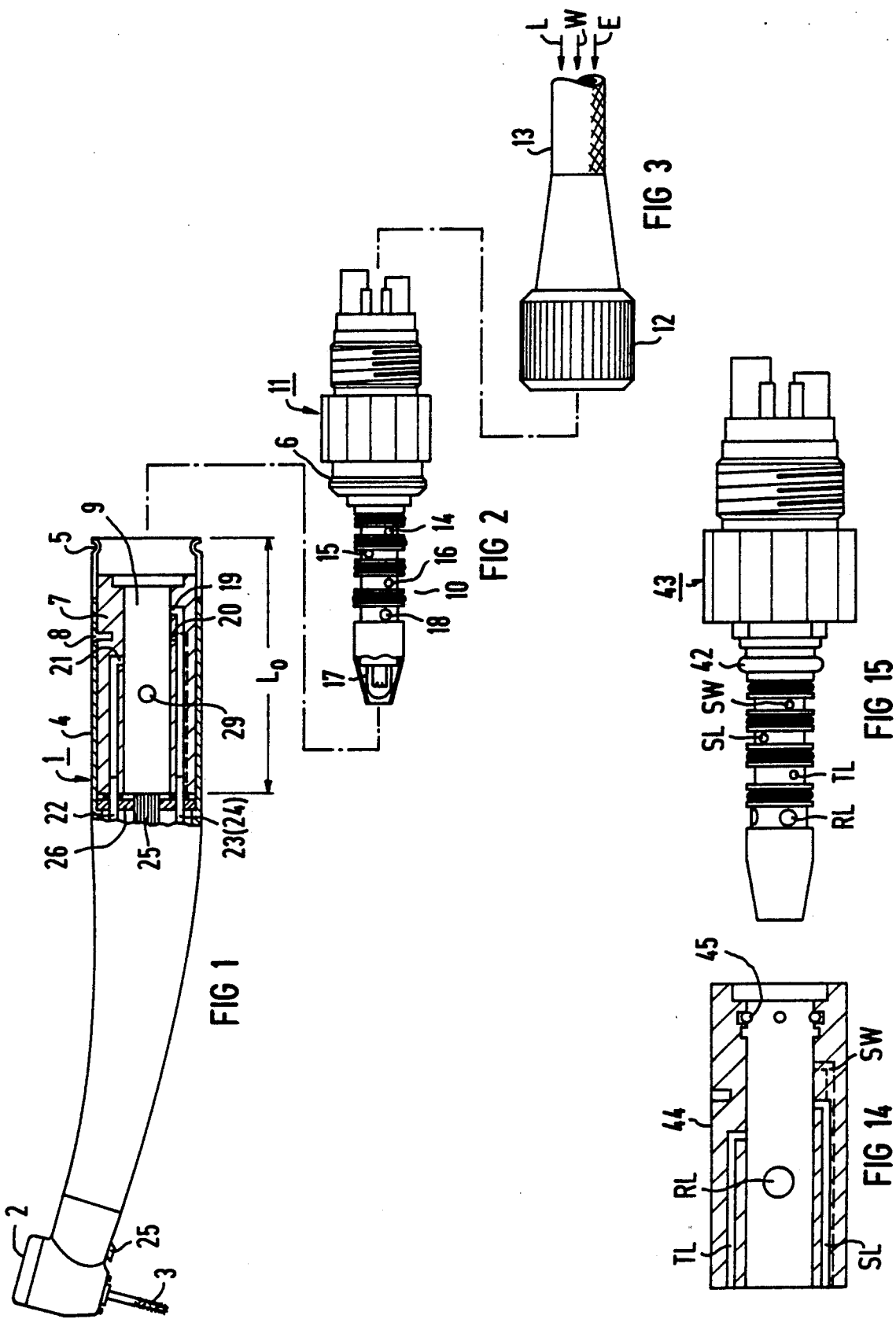

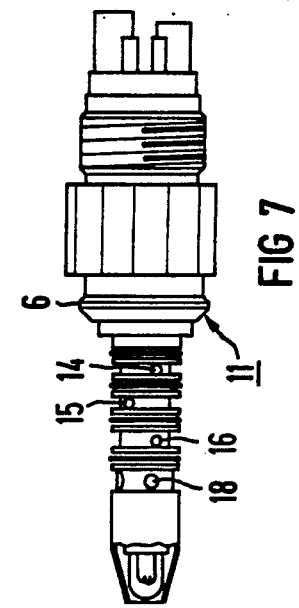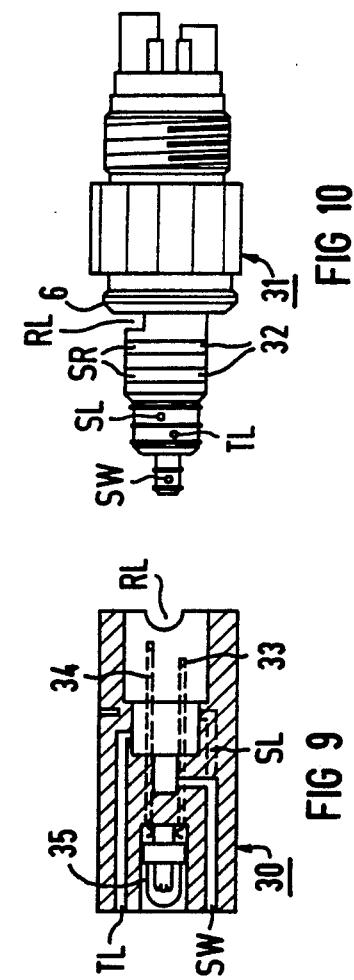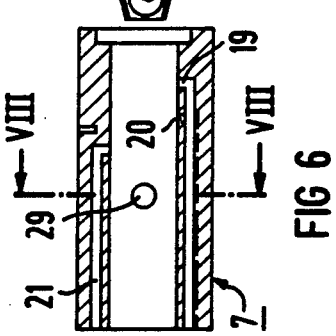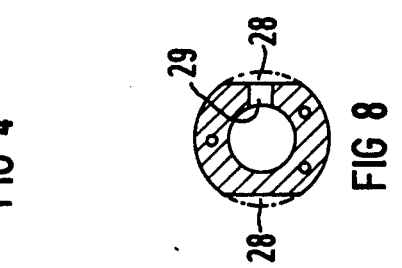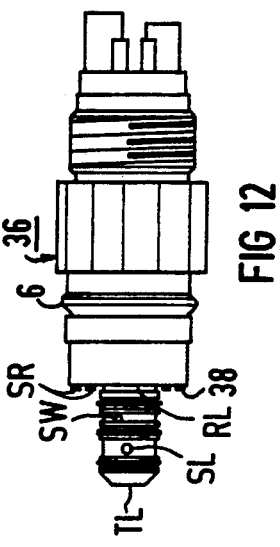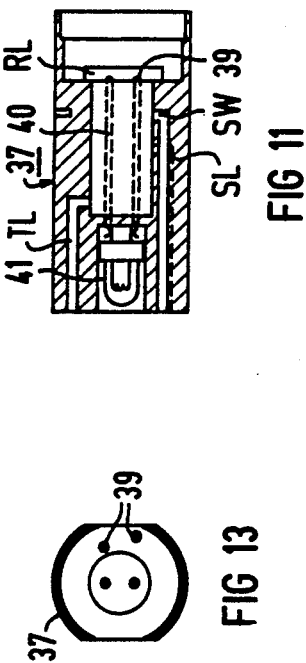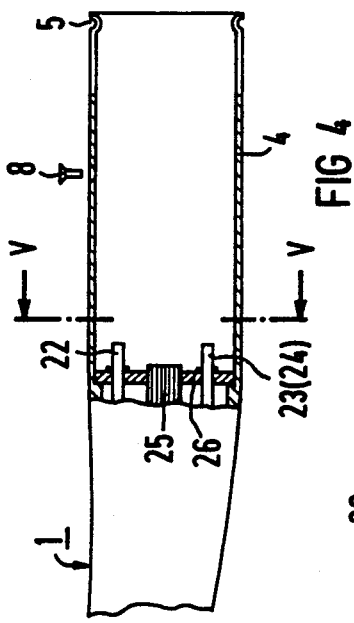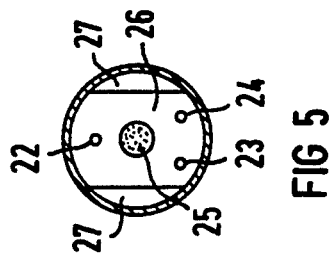

DENTAL HANDPIECE HAVING AN ARRANGEMENT TO FORM COMPATIBLE CONNECTIONS TO DIFFERENTLY DESIGNED ROTATABLE JOINTS

BACKGROUND OF THE INVENTION

The present invention is directed to a dental handpiece comprising means for forming a compatible connection of the handpiece to differently designed rotating joints which deliver different supply media, such as air, water, electrical power and light, and which rotating joints offer these supply media at different locations, said rotating joints being permanently or detachably connectable to a supply hose.

Examples of the various handpieces can be handpieces which are a turbine handpiece, a handpiece which has an air or electrical motor, a handpiece which is a sprayer handpiece or a handpiece for removing dental calculus.

U.S. Pat. No. 4,080,737, whose disclosure is incorporated by reference and which was based on German Patent Application 25 49 177, discloses a coupling mechanism which, in one embodiment, is constructed as a rotating joint. Various handpieces can be operationally coupled to and uncoupled from this rotating joint without the assistance of tools. Voltage or, respectively, light is also offered at the coupling location, in addition to the agents of air and water. A light-conducting element in the form of a light guide is arranged in the center of the joint and a light-forwarding element in the form of an additional light guide is arranged at the end face of the handpiece for transmitting light through the handpiece. When the handpiece and rotating joint are in their coupled condition, the ends of the two light guides are arranged correspondingly opposite one another.

U.S. Pat. No. 4,655,709, whose disclosure is incorporated by reference and which was based on German Application 34 31 052, discloses a coupling mechanism that reveals a possibility of being able to connect turbine handpieces to a rotating joint, wherein both the turbine handpieces have integrated lamps as well as two turbine handpieces having a lamp arranged in the rotating joint. The rotating joint has a peg-shaped or pin-shaped coupling member that is engaged into a correspondingly fashioned receptacle sleeve or socket of the handpiece to form the coupling, which will transfer both the cooling means as well as drive means between the two units. In order to transfer the voltage for feeding the electrical lamp, the rotating joint contains a contact arrangement which has wiper contacts including bands or contact points on the peg-shaped coupling member, which are engaged by terminal contacts of a lamp arranged in the handpiece attachable to the coupling member or the contacts of a lamp arranged in the coupling member or sleeve of the joint.

One advantage of this coupling mechanism is that the turbine handpiece with an integrated lamp, as well as with an externally arranged lamp, can be alternately connectable to one in the same rotating joint, whereby the use of the handpiece can itself easily undertake the replacement of the lamp with a plug-in connection and vice-versa. Since the turbine handpieces are structurally matched to the one rotating joint, it is consequently not possible in the prior art to couple these handpieces to rotating joints that are fashioned with different dimensions.

SUMMARY OF THE INVENTION

The different designs of the rotating joints, which are known in the marketplace, will only fit a specific handpiece, which is usually manufactured by the manufacturer of the joint. In other words, only handpieces of one type are compatible to a specific type or defined rotating joint. An object of the present invention is to create a possibility of providing a handpiece which can be adapted to differently constructed rotary joints without more extensive structural and assembly outlay.

To accomplish the invention, it is possible to provide various inserts for various types of rotating joints, wherein the insert has the inside contour and the conducting passages for the transmission of the drive and cooling agents being suitably aligned to the various ports and outlets of the rotary joint. Thus, the inserts will conduct and transmit the agents to the handpiece, however, these inserts are uniformly adapted to this type of handpiece. As a result thereof, not only can a greater variety of handpieces be paired with different rotating joints, but a uniform rotating joint system is also created in this fashion without the manufacturer of the handpiece having to modify the handpiece design, particularly with reference to the light conduction as well as to the structural design of the rotatable joint.

It is advantageous when the inserts have identical outside diameters, identical lengths and identical hole patterns regarding the transmission of agents with respect to the connection to the handpiece. Given light transmission, it is advantageous when, as known per se, the end of the light guide that carries the light further is engaged in the center of the handpiece and is fed by a lamp that is also centrally arranged in the peg or pin of the rotatable joint. In another conceivable embodiment wherein the voltage is offered at the rotatable joint, it is advantageous when the lamp socket is provided in the insert part and the corresponding connector contacts lead to wiper contacts that contact corresponding wiper rings on the rotatable joint when the sleeve is in the coupled condition thereon. For both embodiments, the light guide that carries the light further can have the same position in the handpiece, regardless of whether the lamp is situated in the rotatable joint or in the insert part, for example the handpiece is absolutely identical for both embodiments whether the lamp is in the joint or in the insert part.

Since the handpiece of different manufacturers are usually differently executed in part with respect to diameter connections and engagement of the handpiece at the rotating joint, it is also advantageous to allocate the connector and catch means for the connection to the rotatable joint to the insert parts. When, as proposed in a further advantageous embodiment, the sleeve-shaped end section of the handpiece is fashioned as a relatively thin sleeve and practically forms only an outer envelope of the handpiece. The handpiece is otherwise filled out by the insert part in this particular region. Then, an especially good dimensional matching to the different diameters of the handpiece and of the rotatable joint to be adapted can be achieved by the insert part.

Other advantages and features of the invention will be readily apparent from the following description of the preferred embodiments, the drawings and claims.

BRIEF DESCRIPTION OF THE DRAWINGS

FIG. 1 is a side view with portions broken away of a dental handpiece in accordance with the present invention;

FIG. 2 is a side view with portions broken away for purposes of illustration of a plug member of a first embodiment of a rotating joint;

FIG. 3 is a side view of a connector part of a supply hose or line;

FIG. 4 is a partial side view with portions broken away with the insert part being removed;

FIG. 5 is a cross sectional view taken along the lines V—V of FIG. 4;

FIG. 6 is a longitudinal cross sectional view of an insert part used with the handpiece of FIG. 1;

FIG. 7 is a side view with portions broken away of the plug member of a rotatable joint used with the insert part of FIG. 6;

FIG. 8 is a cross sectional view taken along the lines VII—VII of FIG. 6;

FIG. 9 is a longitudinal cross sectional view of a second embodiment of an insert part in accordance with the present FIG. 10 is a side view of a plug member of a second type of rotatable joint used with the insert part of FIG. 9;

FIG. 11 is a longitudinal cross sectional view of a third embodiment of an insert part in accordance with the present FIG. 12 is a side view of a third type of plug member of a third type of rotatable joint used with the insert part of FIG. 11;

FIG. 13 is an end view of the right-hand end of the insert part of FIG. 11;

FIG. 14 is a longitudinal cross section of a fourth embodiment of an insert part in accordance with the present invention; and FIG. 15 is a side view of a plug member of a fourth type of rotatable joint used with the insert part of FIG. 14.

DESCRIPTION OF THE PREFERRED EMBODIMENTS

The principles of the present invention are particularly useful when incorporated in a handpiece, generally indicated at 1, which may be a turbine handpiece having a head part 2 containing a pneumatic drive (not shown), such as a turbine, for rotating a tool 3. The pneumatic drive or turbine is of a known type. In a back part of the handpiece 1, which is facing away from the head part 2, the handpiece forms a relatively thin sleeve 4 over a length segment $L_o$ and this sleeve 4 forms practically only an outer jacket of the handpiece. The thin sleeve 4 ends in a resilient molded part 5 at the far end, which will cooperate with an annular collar 6 (see FIG. 2) to form a catch means for axially holding and fixing a plug member, generally indicated at 11, to form a rotatable connection.

An insert part 7 is inserted into the sleeve 4 of the handpiece 1 and is secured against twisting and falling out with the assistance of a suitable fastening part 8 which may be a pin, screw or the like. However, if desired, the part 7 can be axially removed from the handpiece after loosening this fastening part 8. The insert 7 is fashioned largely to be dynamically balanced and contains a central bore 9 for the acceptance of a peg or projection 10 of the plug member 11 for forming the rotatable joint. A supply hose 13 that brings the supply of agents, such as air L, water W and electrical energy E to the rotatable joint can be connected to the plug member 11 with the assistance of a connector fitting 12 (see FIG. 3). The plug member 11 (FIG. 2) has radial bores 14, 15 and 16 for the emergence of spray water, spray air and drive air provided on the peg or projection 10. The bores discharge into annular grooves that are separated by O-rings and, as illustrated, these channels are axially spaced along the pin or projection 10. The electrical energy is connected via lines to an electrical lamp 17 which is arranged at the end face of the peg or pin 10. The pin 10 also has an additional bore 18 through which return air coming from the drive arranged in the handpiece can be conducted into the rotatable joint and from the latter into the open via suitable exit openings.

The insert part 7 (FIG. 1) has channels 19–21 which correspond with the spaced bores 14–16 or are in contact with the channels of these bores, and the conduit or channels 19–21 will accept the agents of the spray water, the spray air and the drive air from the plug member. The conduit channels accept the agent from the peg or projection 10 and then conduct them to one end face of the insert part 7. In a known fashion, the agents are then conducted from the one end face of the insert part to the head part 2 of the handpiece by lines, such as 22, 23 and 24. The handpiece 1 also has a light guide 25 which, together with the ends of the lines 22, 23 and 24, are held in a mount 26. This mount 26, as illustrated in FIG. 5, is constructed to provide openings 27 for carrying return air alongside the sleeve. In other words, the openings 27 are formed by flats provided on the circular configuration of the mount 26. Corresponding flow-through openings or, respectively, channels 28 (see FIG. 8) are also formed between the insert part 7 and the sleeve part 4 by providing flattened portions on both sides of the insert part (see FIGS. 6 and 8). The return air can, thus, flow back between the outside sleeve 4 of the handpiece and the insert part 7 and then can ultimately be conducted through a cross bore 29 (see FIG. 8) to enter a channel in communication with the bore 18 of the pin 10.

The sections of the channels or lines, that carry the individual agents, are connected to one another in the assembled condition of the insert part 7, in the sleeve 4 and in the plugged-in condition of the plug member 11 in the bore 9. Appropriate seal elements are provided at each of the respective junctions to seal the agents from one another. As illustrated, these seal elements are O-rings.

FIGS. 6 and 7; 9 and 10; and 11 and 12, show combinations of insert parts and plug members for different types of rotary joints, which part and plug member will mate with one another. The combinations have in common that the insert part is always adapted to be received in the sleeve 4 of the handpiece 1 with respect to the outer contour and shape, but has an inside contour and shape that allows agent transfer locations which are different and are matched to the respective plug portions of each of the different rotatable joints.

Instead of the insert part 7 that has been described above, an insert part 30 (FIG. 9) can also be introduced into the handpiece 1. This insert part 30 will mate with a plug member 31 of a second type of rotary joint, which plug member is illustrated in FIG. 10. A comparison will show that the plug member 31 is fashioned structurally different than the plug member 11 of FIG.

7 with respect to the pin formation, as well as with respect to the offering of the various agents. Another difference is the electrical contacts are in the form of wiper rings SR, shown by bands 32 which are arranged on the circumference of the peg or pin and are present in the plug member 31. These rings 32 will cooperate with corresponding resilient contact elements 33 of the insert part 30. The contact elements 33 are connected by lines 34 to a socket for a lamp 35 which is mounted in the insert part 30. As illustrated, the plug member 31 has a pin with variable diameter portions with the smallest portion having a port for release of the spray water SW, whereas the intermediate diameter portion has axially spaced ports for the drive air DL and the spray air SL. The larger diameter port, besides having the bands 32 to form the wiper rings SR, also has a port or exit RL for the return air. Thus, it can be seen that the agents, such as RL, SL, TL and SW are offered at different locations than in the embodiment of the plug member 11 of FIG. 7. However, the structure of the insert part 30 has outlet ports for these agents TL, SL and SW, which ports are positioned in the end which will coact with the lines, such as 22, 23 and 24, which are held by the member 26 in the sleeve 1.

In contrast to the embodiment set forth above wherein the lamp 17, as a light-producing element, is arranged at the end face of the pin of the plug member 11, the lamp 35 of the second embodiment is a component part of the insert part 30 and receives the required voltage via contact arrangements 32 and 33 in the form of wiper rings 32 and resilient contacts 33.

Since the outer dimensions, such as the length and diameter of the insert part 30, are identical to the insert part 7 of FIG. 6, the part 30 can be introduced into the handpiece in place of the insert part 7.

FIGS. 11 and 12 show a third combination of a rotatable joint having a plug member 36 and insert part 37. It proceeds from the illustration that the plug member 36 is fashioned structurally different and offers the agents TL, SL, SR, SW, and RL at other locations than do the previously mentioned embodiments. Accordingly, the insert part 37 is also fashioned such that the lines and channels, although they accept the agents at different locations, nonetheless, have their output or outlet ports in the same position or location at the end face as in the previously mentioned embodiments, since the same hole pattern for the output of the agents is present. Thus, the insert part 37 can be introduced in the handpiece 1 in place of either the insert part 30 or the insert part 7 and the agents TL, SW and SL can be conducted to the handpiece via the channels 22, 23 and 24 in the same way as set forth above. Since wiper rings SR are not provided on the circumference of the pin of the plug member 36, but are provided on a surface 38, which forms an end face, the insert part 37 contains resilient contact pins 39 which are arranged on two different diameters to contact the wiper rings SR which are formed on the surface 38 of the plug member 36. The contact pins 39 are connected by lines 40 to a lamp 41 which is again arranged in the center of the part 37.

As may be seen from the illustrations, a handpiece 1 receives an insert part, whether it is 7, 30 or 37, which is matched to the respective plug member 11, 31 or 36 of the particular rotating joint. Without having to be structurally modified, the handpiece can be refitted for employment with a different rotatable joint merely by replacing the insert part.

It has been assumed in the embodiments set forth above that the rotatable part can be held by identical holding and catch means which is formed by the parts 5 and 6 for an axial securing of the handpiece in its coupled condition. If this is structurally not possible or not established, then it is advantageous to, likewise, also provide the insert part with catch means for holding the handpiece to the plug member of the rotatable joint and its respective part. An embodiment shown in FIGS. 14 and 15 is a modification of the parts shown in FIGS. 6 and 7, namely to such an extent that the annular collar 42 for locking a plug member 43 has a smaller diameter than the collar 6 of the embodiment shown in FIG. 7. As a result thereof, the rotatable joint will not lock directly to the handpiece 1. In order to enable a latching in such a case, it is proposed that a modified insert part 44 containing means for latching, for example in the form of known ball catches 45, is provided. In this version, the handpiece is independent with respect to the structural design of the rotatable joint insofar as it relates to the agent guidance, but is also independent with respect to the latching of the handpiece to the plug member of the rotatable joint. In this version, accordingly, the handpiece is even more neutral and more independent of the structure of the rotatable joint being used.

Although various minor modifications may be suggested by those versed in the art, it should be understood that I wish to embody within the scope of the patent granted hereon all such modifications as reasonably and properly come within the scope of my contribution to the art.

I claim:

1. A dental handpiece having means for forming a compatible connection to differently design rotatable joints with different plug members that deliver different supply agents selected from air, water, electrical current and light, a rotatable joint being connectable to a supply hose, said means for forming compatible connection including an insert part of a plurality of insert parts, said handpiece having a sleeve-shaped end section at an end facing away from a head part for receiving said insert part, said insert part having an interior matched to one of the plug members of a rotatable joint for forming a rotatable connection therewith and enabling a transfer of agents from said plug member to the insert part, each of the insert parts having an exterior being matched to the interior of a sleeve portion of the dental handpiece, said exterior having outlet ports for communication to lines of said handpiece, said outlet ports being identically positioned for each of the insert parts so that by changing the insert part, the handpiece can be connected to a different type of rotatable joint which has a different configuration and shape.

2. A dental handpiece according to claim 1, wherein the end section of the handpiece forms a thin sleeve that forms only an outer envelope and all agent conducting lines are arranged in the insert part.

3. A dental handpiece according to claim 2, wherein the outlet ports for agent transfer from the insert part to the handpiece are provided at one end face of the insert part which is directed toward the head part.

4. A dental handpiece according to claim 3, wherein one of the insert parts contains a centrally arranged lamp on said one end face, said lamp having electrical contacts which are connected to a contact arrangement arranged at the end of the insert part that faces away from the head part, said contact arrangement corresponding with wiper ring contacts provided on a plug member of the particular rotatable joint.

5. A dental handpiece according to claim 4, wherein the handpiece contains a light guide that ends centrally facing towards the insert part and is in a coupled condition with the lamp carried by the insert part.

6. A dental handpiece according to claim 5, wherein the handpiece has a mount for providing a fixing of the end of the light guide facing away from the head part, said mount forming flow-through openings which cooperate with the sleeve-shaped end section of the handpiece for guiding return air.

7. A dental handpiece according to claim 6, wherein said flow-through openings form segment-shaped cross sections.

8. A dental handpiece according to claim 6, wherein each of the insert parts have flow-through channels for the return air that mate with said flow-through openings of the mount.

9. A dental handpiece according to claim 8, wherein each of the insert parts has a dynamically balanced inside contour.

10. A dental handpiece according to claim 1, wherein the handpiece contains a light guide that has an end centrally facing towards an insert part, said insert part having a central bore receiving the plug member, said plug member having a lamp which is positioned opposite said end of the light guide when the plug member is received in a coupled condition with said insert part.

11. A dental handpiece according to claim 10, which includes a mount for fixing the end of the light guide adjacent the insert part, said mount having segment-shaped openings forming a flow-through opening for guiding return air to said insert part.

12. A dental handpiece according to claim 11, wherein the insert part has channels formed on an exterior thereof corresponding to the flow-through openings of said mount.

13. A dental handpiece according to claim 10, wherein the insert part comprises dynamically balanced inside contours.

14. A dental handpiece according to claim 1, which includes a light guide having an end centrally facing towards the insert part, said insert part having a lamp arranged in the end facing said head part aligned with the end of said light guide.

15. A dental handpiece according to claim 14, wherein the insert part has dynamically balanced interior contours.

16. A dental handpiece according to claim 14, wherein the insert part has contact members received on an internal bore for engaging slip rings provided on a plug member of said rotatable joint, said contact members being connected to said lamp.

17. A dental handpiece according to claim 14, wherein the insert has a resilient contact arrangement on an end face for engaging slip rings provided on an end face of the plug member forming the rotatable coupling, said contact arrangement being connected to said lamp.

* * * * *